United States Patent [19]

Mori et al.

[11] Patent Number: 4,871,869
[45] Date of Patent: Oct. 3, 1989

[54] OPTICALLY ACTIVE BICYCLO[3.3.0]OCTANE AND PROCESSES FOR THE PREPARATION THEREOF

[75] Inventors: Kenji Mori, Tokyo; Masahiro Tsuji, Saitama, both of Japan

[73] Assignee: Nisshin Flour Milling Co., Ltd., Tokyo, Japan

[21] Appl. No.: 293,414

[22] Filed: Jan. 4, 1989

[30] Foreign Application Priority Data

Jan. 6, 1988 [JP] Japan .................................. 63-339
Jan. 6, 1988 [JP] Japan .................................. 63-340

[51] Int. Cl.$^4$ .............................................. C07F 7/08
[52] U.S. Cl. ................................ 556/436; 549/214
[58] Field of Search ......................... 556/436; 549/214

[56] References Cited

U.S. PATENT DOCUMENTS

| | | | |
|---|---|---|---|
| 4,359,581 | 11/1982 | Skuballa et al. | 556/436 X |
| 4,554,363 | 11/1985 | Vorbrueggen | 556/436 X |
| 4,644,068 | 2/1987 | Shibasaki et al. | 556/436 X |
| 4,681,951 | 7/1987 | Shibasaki et al. | 556/436 X |
| 4,762,936 | 8/1988 | Shibasaki et al. | 556/436 X |

FOREIGN PATENT DOCUMENTS 0216585  4/1987  European Pat. Off. ............ 556/436
0141986  6/1988  Japan ................................... 556/436

*Primary Examiner*—Paul F. Shaver
*Attorney, Agent, or Firm*—Cushman, Darby & Cushman

[57] ABSTRACT

New intermediate, an optically active (1R,5S,6S,7R)-6-tert-butyldiphenylsilyloxmethyl-7-hydroxy-bicyclo[3.3.0]octan-3-one (I) having high optical purity which is useful for the synthesis of an optically active carbacyclin and an optically active pentalenolactone E methyl ester. The compound (I) is also an intermediate compound serving for the purpose of improving the optical purity of (1R,5S,6S,7R)-3,3-ethylenedioxy-6-hydroxymethyl-7-(2'-tetrahydropyranyloxy)bicyclo[3.3.0]octane. The compound (I) is prepared by reacting (1R,5S,6S,7R)-3,3-ethylenedioxy-6-hydroxymethyl-7-(2'-tetrahydropyranyloxy)bicyclo[3.3.0]octane with tert-butylchlorodiphenylsilane in the presence of a base and removing the ethylenedioxy and tetrahydropyranyl groups of the resultant compound under an acid condition.

3 Claims, No Drawings

OPTICALLY ACTIVE BICYCLO[3.3.0]OCTANE AND PROCESSES FOR THE PREPARATION THEREOF

FIELD OF THE INVENTION

This invention relates to a new compound, (1R,5S,6S,7R)-6-tert-butyldiphenylsilyloxymethyl-7-hydroxybicyclo[3.3.0]octan-3-one which is useful as an intermediate for the synthesis of an optically active carbacyclin and an optically active pentalenolactone E methyl ester and a process for the preparation thereof.

BACKGROUND OF THE INVENTION

Prostacyclin (PGI$_2$) of the following structure is of various pharmacological effects including blood platelet agglutination inhibitory activity and vasodilation activity, and is considered to be promising for development of medicine. However, prostacyclin has such a drawback, on the other hand, that it is a very unstable compound.

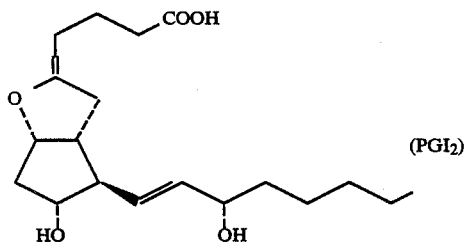

(PGI$_2$)

Of the prostacyclin derivatives, carbacyclin (called 9(0)-methanoprostacyclin) of the following formula (XVII) has been known to be a chemically stable compound in which the oxygen atom of enol ether moiety of prostacyclin (PGI$_2$) is substituted with a methylene group.

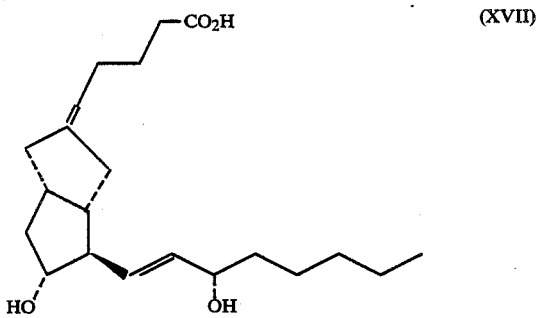

(XVII)

Processes for the synthesis of an optically active carbacyclin have been disclosed, for example, in "Tetrahedron", Vol. 37, 4391 (1981), "Journal of Organic Chemistry", Vol. 44, 2880 (1979) and "Journal of Organic Chemistry", Vol. 46, 1954 (1981). However, these processes are of the disadvantage of lengthy step. Furthermore, processes for the synthesis of the above-mentioned carbacyclin using as an intermediate (1SR,5RS)-2-ethoxycarbonyl-7,7-ethylenedioxybicyclo[3.3.0]octan-3-one represented by the following formula (VIII) are disclosed, for example, in "Tetrahedron Letters", 3743 (1978), "Journal of Chemical Society, Chemical Communication", 1067 (1978) and "Tetrahedron Letters", 433 (1979).

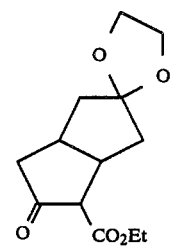

(VIII)

However, the products obtained by the above-mentioned processes are racemic compounds, i.e., the (1SR,5RS) epimers which do not exhibit optical activity. That is, since the intermediates used in these processes are racemic compounds, the products obtained thereby are necessarily racemic compounds. Accordingly, if the optically active (1S,5R) compound can be used as the intermediate in the above-mentioned processes, it follows that the optically active carbacyclin referred to above is obtained quite conveniently.

It has been known in this connection that the above-mentioned intermediate, the compound of the following formula (VIII) is prepared from cis-bicyclo[3.3.0]octane-3,7-dione of the following formula (V) according to the following scheme as taught in the above-mentioned "Journal of Chemical Society, Chemical Communication", 1067 (1978) and "Tetrahedron Letters", 433 (1979).

SCHEME

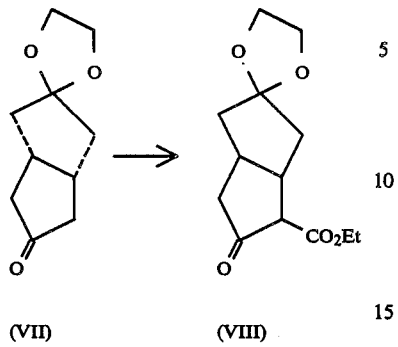
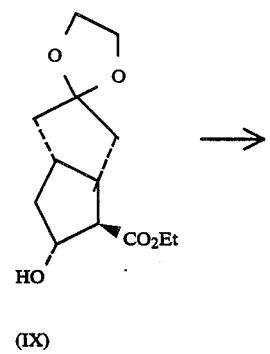

(VII)　　　　(VIII)

As can be seen from the above scheme, the compound of the formula (VIII) which is formed by introduction of an ethoxycarbonyl group into the compound of the formula (VII) always becomes a racemic compound which does not have optical activity.

Under such circumstances, we have proposed in Japanese Patent LOP Publn. No. 280294/1986 as a method of isolating only the (1S,5R)epimer from the racemic compound of formula (VIII) a process wherein said racemic compound, (1SR,5RS)-2-ethoxycarbonyl-7,7-ethylenedioxy-bicyclo[3.3.0]-octan-3-one is treated with a microorganism having an ability of specifically reducing the keto group of the (1R,5S)epimer of the racemic compound (VIII) to afford, as a non-reduced compound, optically active (1S,5R)-2-ethoxy-carbonyl-7,7-ethylenedioxybicyclo[3.3.0]octan-3-one of formula (IV)

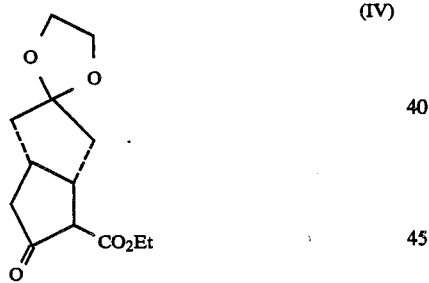

(IV)

The optically active (1S,5R)-2-ethoxycarbonyl-7,7-ethylenedioxybicyclo[3.3.0]octan-3-one of formula (IV) as prepared above can be allowed to lead to an optically active carbacyclin according to the following reaction scheme.

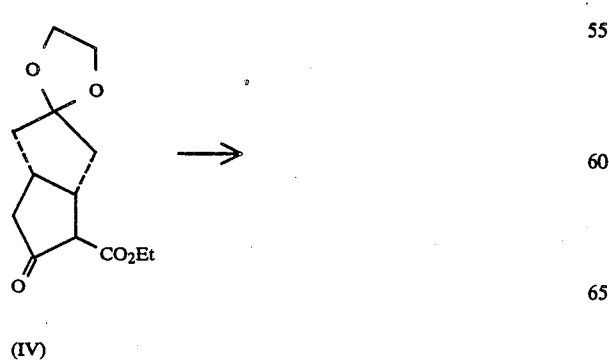

(IV)

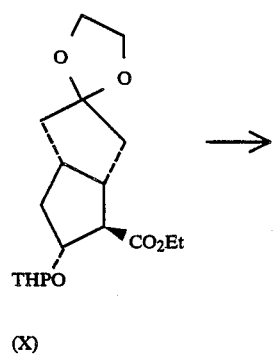

(IX)

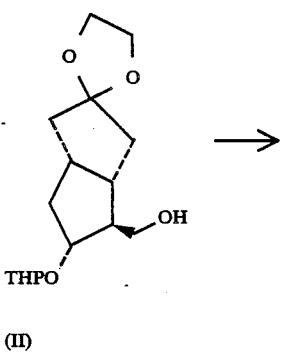

(X)

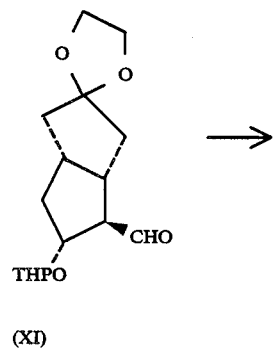

(II)

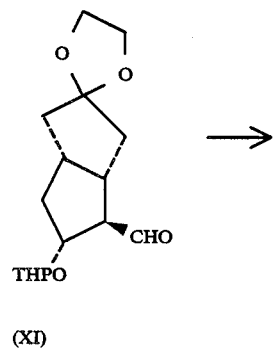

(XI)

-continued

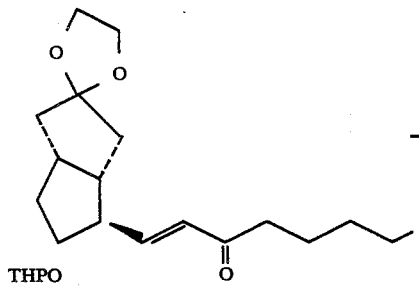

(XII)

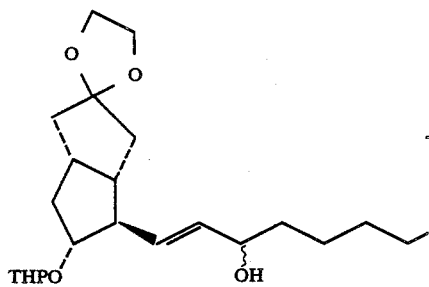

(XIII)

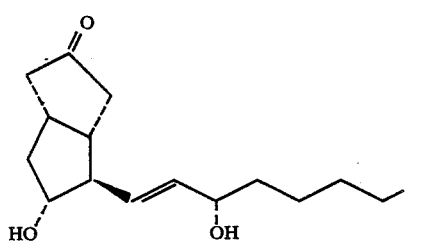

(XIV)

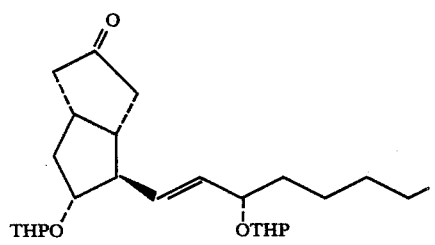

(XV)

-continued

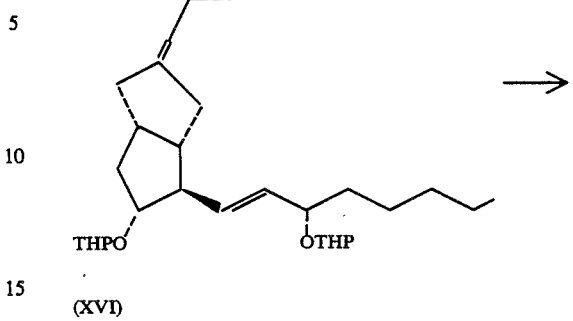

(XVI)

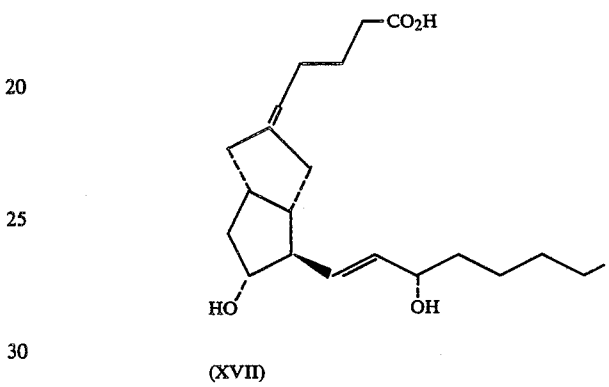

(XVII)

The optical purity of optically active (1S,5R)-2-ethoxycarbonyl-7,7-ethylenedioxybicyclo[3.3.0]octan-3-one of formula (IV) which is prepared by treating (1SR,5RS)-2-ethoxycarbonyl-7,7-ethylenedioxybicyclo[3.3.0]octan-3-one of formula (VIII) with the microorganism according to our previously proposed method may be varied depending on kinds of the microorganism used, but is 92 to 94% e.e. (enantiomer excess) with the best result using Saccharomyces bailii, and the optical purity of the end product, carbacyclin [compound of formula (XVI)]prepared by using the compound of formula (IV) as obtained above is approximately 96% e.e. Where. baker's yeast is used which is inexpensive and most easily available as a microorganism, the optical purity of the resultant compound (IV) is about 60% e.e. and that of carbacyclin obtained with this compound (IV) is still not satisfactory.

On one hand, the intermediates produced in the reaction route starting from the compound of formula (IV) and leading to carbacyclin of formula (XVII) are respectively poor in crystallinity which does not permit the improvement in the optical purity by means of recrystallization. In this situation, a starting material having high optical purity has been needed for the synthesis of carbacyclin.

DETAILED DISCLOSURE OF THE INVENTION

Now, we have investigated bicyclo[3.3.0]octanes with good crystallinity serving as the intermediates for the synthesis of carbacyclin and found that a new compound of formula (I), (1R,5S,6S,7R)-6-tert-butyldiphenylsilyloxy- methyl-7-hydroxybicyclo[3.3.0]octan-3-one is of very good crystallinity and this compound can be subjected to a recrystallization treatment to provide markedly improved optical purity.

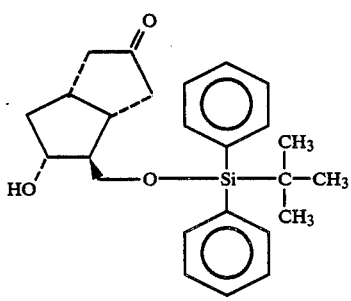 (I)

The compound of formula (I) can be readily prepared by reacting (1R,5S,6S,7R)-3,3-ethylenedioxy-6-hydroxymethyl7-(2'-tetrahydropyranyloxy)bicyclo[3.3.0]octane of formula (II)

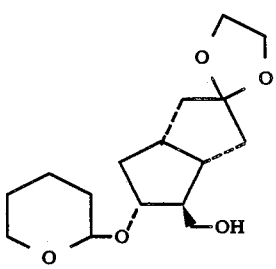 (II)

with tert-butylchlorodiphenylsilane in the presence of a base to form (1R, 5S, 6S, 7R)-6- tert-butyldiphenyl-silyloxymethyl-3,3-ethylenedioxy-7-(2'-tetrahydropyranyloxy)bicyclo[3.3.0]octane of formula (III)

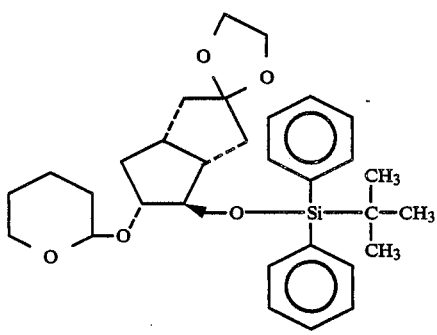 (III)

and removing the ethylenedioxy and tetrahydropyranyl groups of the resultant compound under an acid condition. Further, the compound of formula (I) as prepared above can be subjected to a recrystallization treatment to improve the optical purity. Subsequently, the compound (I) having improved optical purity can be used for recycle as a starting compound for the synthesis of (1R,5S,6S,7R)-3,3-ethylene-dioxy-6-hydroxymethyl-7-(2'-tetrahydropyranyloxy)bicyclo-[3.3.0]octane of formula (II), with the result of the improved optical purity of the compound (II).

Thus, the present invention also includes a process of preparing (1R,5S,6S,7R)-3,3-ethylenedioxy-6-hydroxymethyl7-(2'-tetrahydropyranyloxy)bicyclo[3.3.0]octane having improved optical purity of formula (II)

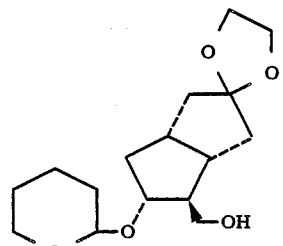 (II)

which comprises reacting (1R,5S,6S,7R)-3,3-ethylenedioxy-6-hydroxymethyl-7-(2'-tetrahydropyranyloxy)-bicyclo[3.3.0]octane of formula (II)

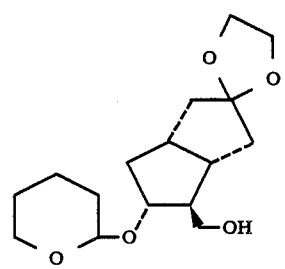 (II)

with tert-butylchlorodiphenylsilane in the presence of a base to form (1R,5S,6S7R)-6-tert-butyldiphenylsilyloxymethyl-3,3-ethylenedioxy-7-(2'-tetrahydropyranyloxy)bicyclo[3.3.0]octane of formula (III),

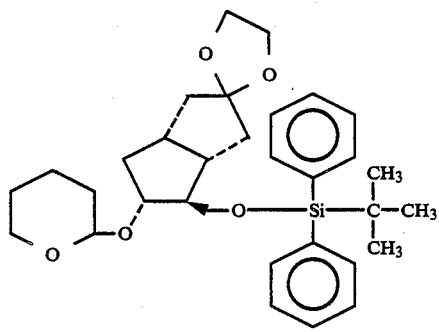 (III)

removing the ethylenedioxy and tetrahydropyranyl groups of the resultant compound under an acid condition to form (1R,5S,6S,7R)-6-tert-butyldiphenylsilyloxymethyl-7-hydroxybicyclo[3.3.0]octan-3-one of formula (I), subjecting the resultant compound to a recrystallization treatment to improve the optical purity, protecting the compound having improved optical purity at the 3- and 7-positions respectively with the ethylenedioxy and tetrahydropyranyl groups to form (1R,5S,6S,7R)-6-tert-butyldiphenylsilyloxy- methyl-3,3-ethylenedioxy-7-(2'-tetrahydropyranyloxy)bicyclo-[3.3.0]octane of formula (III) and removing the tert-butyldiphenylsilyl group of the resultant compound in the presence of a fluorine anion.

As stated above, (1R,5S,6S,7R)-6-tert-butyldiphenylsilyloxymethyl-7-hydroxybicyclo[3.3.0]octan-3-one of the invention is an intermediate compound serving for the purpose of improving the optical purity of (1R,5S,6S,7R)-3,3-ethylenedioxy-6-hydroxymethyl-7-(2'-tetrahydropyranyloxy)bicyclo[3.3.0]octane and further this compound itself is also useful as an intermediate for the synthesis of optically active pentalenolactone E methyl ester as shown in the following reaction scheme.
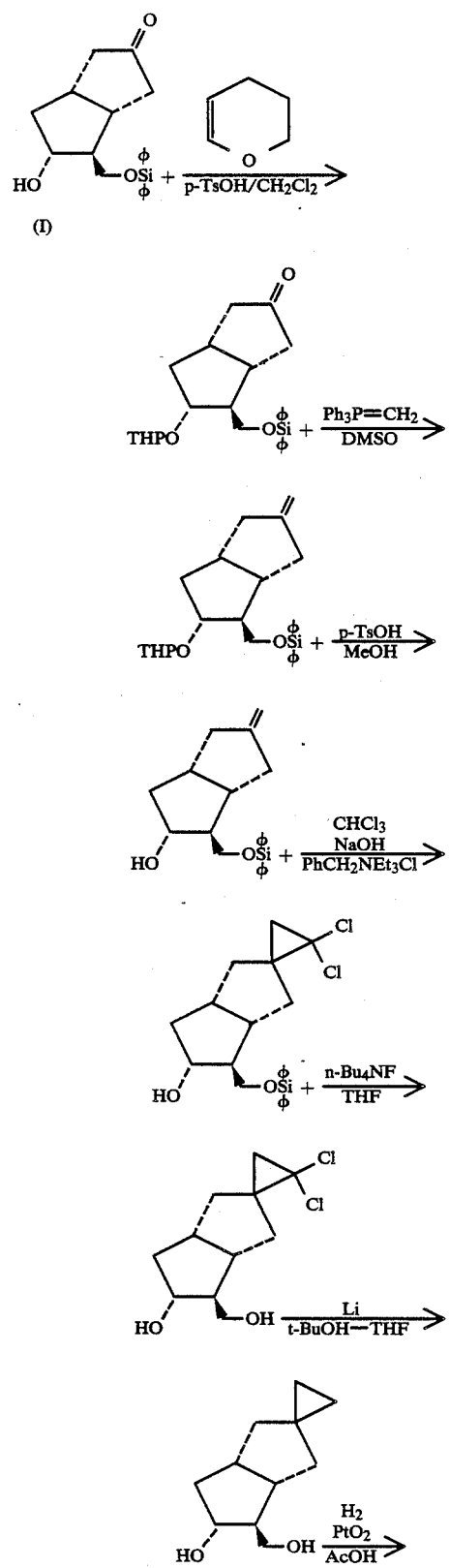
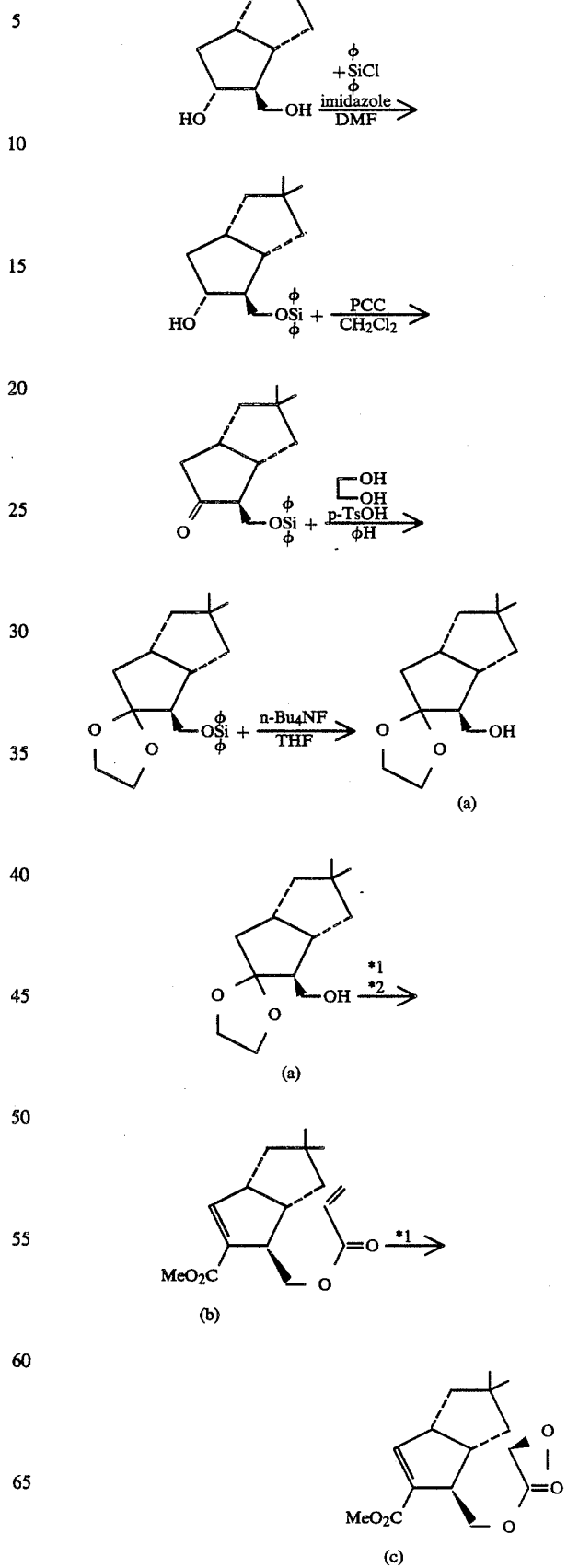

*1 D. E. Cane and P. J. Thomas, J. Am. Chem. Soc. 106, 5295 (1984)
*2 L. A. Paquette, G. D. Annis and H. Schostarez, J. Am. Chem. Soc. 104, 6646 (1982)

The reaction between the compound of formula (II) and tert-butylchlorodiphenylsilane is conveniently carried out in a solvent, preferably an inert solvent and at a temperature between 0° and 100° C, preferably between 10° and 40° C, using 1.0 to 4 mols, preferably 1.1 to 1.5 mols of tert-butylchlorodiphenylsilane per mol of the compound of formula (II). This reaction is also conducted in the presence of a base. The bases which may be used in the reaction include e.g., dimethylamine, diethylamine, diisopropylamine, trimethylamine, triethylamine, imidazole, pyridine, piperidine, piperazine or the like. Inert solvents which may preferably be used in the reaction include N,N'-dimethylformamide, acetonitrile, methylene chloride or the like.

The reaction may typically proceed under the reaction condition ordinarily performed in N,N'-dimethylformamide at room temperature in the presence of imidazole.

Subsequent removal of the ethylenedioxy and tetrahydropyranyl groups is carried out under the condition wherein both protecting groups can be removed. Such condition includes the reaction performed in water, tetrahydrofuran or a mixed solution of water and tetrahydrofuran and at a temperature between 0° and 100° C., preferably between 50° and 80° C., using as an acid, acetic acid, hydrochloric acid, sulfuric acid, p-toluenesulfonic acid, etc.

The resultant (1R,5S,6S,7R)-6-tert-butyldiphenylsilyloxymethyl-7-hydroxybicyclo[3.3.0]octan-3-one of formula (I) is of good crystallinity and can be readily separated as a crystalline solid from a reaction mixture by condensing the mixture. Other separation methods e.g., column chromatography are also applicable.

The compound of formula (I) thus separated may further be subjected to a recrystallization treatment to improve the optical purity. Conventional methods which may be used in recrystallization of the compounds are applicable. These methods include dissolving under heat the compound in a suitable solvent and allowing to cool the resultant supersaturated solution or dissolving the compound in a suitable solvent, distilling off a part of the solvent to prepare a supersaturated solution and separating out the desired crystals from the solution, or the like. Preferably, such recrystallization is carried out by dissolving the compound in a soluble solvent such as ethyl acetate, ether, acetone, ethanol, benzene, etc. and adding to a solution a non-soluble solvent such as hexane, petroleum ether, etc. to effect crystallization.

The optical purity of the compound of formula (I) can be increased by recrystallization. For instance, the compound having 40% e.e. of the optical purity can be recrystallized twice to afford that having more than 98% e.e. 70 to 80% e.e. can be recrystallized once to more than 98% e.e. Recrystallization of the compound (I) having more than 98% e.e. of the optical purity can afford that having about 100% e.e.

The compound of formula (I) increased in optical purity by such recrystallization treatment is converted to (1R,5S,6S,7R)-3,3-ethylenedioxy-6-hydroxymethyl-7-(2'-tetrahydropyranyloxy)bicyclo[3.3.0]octane by protecting the 3-keto group with ethylenedioxy group and the 7-hydroxyl group with tetrahydropyranyl group, followed by removal of tert-butyldiphenylsilyl group in the presence of a fluorine anion.

Protection of the 3-keto group with ethylenedioxy group is carried out by conventional methods. For example, this may be conducted by reacting the compound of formula (I) with ethylene glycol in a suitable organic solvent, e.g., a hydrocarbon solvent such as benzee, toluene, etc. in the presence of an acid catalyst such as p-toluenesulfonic acid, oxalic acid, adipic acid, acetic acid, pyridinium p-toluenesulfonate, hydrochloric acid, sulfuric acid, etc. This reaction is preferably carried out while removing water producing at the boiling temperature of the solution, e.g., by azeotropic distillation. Alternatively, this reaction is performed by acetal exchange. Such acetal exchange is conducted by reacting the compound of formula (I) with 1,3-dioxolans such as 2-methoxy-1,3-dioxolan, 2-ethyl-2-methyl-1,3-dioxolan, etc. at a temperature between 20° and 120° C. in the presence of said acid catalyst with or without a solvent such as benzene, toluene, etc.

The compound protected at the 3-position with ethylenedioxy group is subsequently protected at the 7-hydroxyl group with tetrahydropyranyl group. Protection of the 7-hydroxyl group is also carried out by conventional methods. For example, this may be conducted by reacting the compound protected at the 3-position with ethylenedioxy group, with dihydropyran in a suitable organic solvent e.g., methylene chloride, ether, etc. in the presence of a catalyst e.g., pyridium p-toluenesulfonate, p-toluenesulfonic acid, etc. This reaction is carried out, for example, at a temperature between 10° and 40° C.

Subsequently, the tert-butyldiphenylsilyl group in the compound protected at the 3- and 7-positions is removed for conversion to hydroxymethyl group. This reaction is also carried out by conventional methods e.g., by treating said protected compound with fluorinated tetrabutylammonium or fluorinated pyridinium in a suitable organic solvent e.g., tetrahydrofuran at a temperature between 10° and 40° C.

In the manner as mentioned above, the compound of formula (II) is converted to that of formula (I) which is further recrystallized to increase the optical purity. The compound (I) having improved optical purity can be used for recycle as a starting material for the synthesis of the compound of formula (II), which results in improved optical purity of the compound (II).

The present invention is further illustrated by the following non-limitative examples and referential examples.

REFERENTIAL EXAMPLE 1
(1S,5R)-2-Ethoxycarbonyl-7,7-ethylenedioxy-bicyclo [3.3.0]octan-3-one (IV)

To a solution of 100 ml of 0.1 M phosphate buffer (pH 7) containing sucrose (15 g) was dispersed 7.0 g of baker's yeast at 30° C., and the mixture was shaken at 30° C. for 15 minutes. To the resulting mixture was added an emulsion of 505 mg of (1SR,5RS)-2-ethoxycarbonyl-7,7-ethylenedioxybicyclo[3.3.0]octan-3-one (VIII) in 0.2% Triton X-100 solution (15 ml), and the mixture was shaken at 30° C. After 8 hours, 10 g of sucrose were added to the mixture. After shaking for 24 hours, the reaction mixture was filtered through Celite, the filtrate was saturated with sodium chloride and extracted three times with ethyl acetate. The organic layer was washed with saturated brine, dried over sodium sulfate, and concentrated. The residue was purified by silica gel chromatography (eluting solution: 20% (v/v) diethyl ether/hexane) to obtain 183 mg of oily (1S,5R)-2-ethoxycarbonyl-7,7-ethylenedioxybicyclo[3.3.0]octan-3-one, (IV).

Specific rotation: $[\alpha]_D^{21}15.3°$ (c=1.87, CHCl$_3$).

Infrared absorption (liquid-film method)(cm$^{-1}$): 1765, 1735, 1665, 1625.

REFERENTIAL EXAMPLE 2

(1R,5S,6R,7R)-6-Ethoxycarbonyl-3,3-ethylenedioxy-7-hydroxybicyclo[3.3.0]octane (IX)

To a stirred solution of 2.09 g of (1S,5R)-2-ethoxycarbonylbicyclo-7,7-ethylenedioxy[3.3.0]octan-3-one (IV) having $[\alpha]_D^{21}+15.3°$ (c=1.87, CHCl$_3$) in 21 ml of ethanol was added at −40° C. over 30 minutes 0.17 g of sodium borohydride. The mixture was stirred for 1 hour. After removal of ethanol in vacuo, the residue was diluted with water and extracted with ethyl acetate. The organic layer was washed with saturated brine, dried over sodium sulfate, and concentrated. The residue was purified by silica gel chromatography (eluting solution: 20–50% (v/v) diethyl ether/hexane) to obtain 1.60 g of the oily title compound.

Infrared absorption spectrum (liquid-film method) (cm$^{-1}$): 3500, 1730

REFERENTIAL EXAMPLE 3

(1R, 5S, 6S, 7R)-3,3-Ethylenedioxy-6-hydroxymethyl-7-(2'-tetrahydropyranyloxy)bicyclo[3.3.0]octane (II)

A mixture of 2.65 g of (1R,5S,6R,7R)-6- ethoxycarbonyl-3,3-ethylenedioxy-7-hydroxybicyclo[3.3.0]octane (IX), 1.34 g of dihydropyrane, 0.26 g of pyridinium p-toluenesulfonate in 30 ml of anhydrous methylene chloride was stirred at room temperature for 3 hours. Then, the reaction mixture was successively washed with saturated aqueous sodium hydrogencarbonate solution and saturated brine, dried over sodium sulfate, and concentrated to obtain as the residue 3.70 g of oily tetrahydropyranyl ether. A solution of the resulted crude tetrahydropyranyl ether in 15 ml of anhydrous diethyl ether was added dropwise over 1 hour to a stired and ice-cooled suspension of 0.59 g of lithium aluminum hydride in 50 ml of anhydrous diethyl ether. The mixture was further stirred at room temperature for 30 minutes. After ice-cooling, to the reaction mixture was added successively 0.6 ml of water, 1.8 ml of 10% aqueous sodium hydroxide solution and 0.6 ml of water, and the mixture was further stirred for 1 hour. The mixture was filtered through Celite, dried over sodium sulfate, and concentrated. The residue was purified by silica gel chromatography (eluting solution: 25% (v/v) ethyl acetate/hexane) to obtain 3.04 g of the oily title compound.

Infrared absorption spectrum (liquid-film method) (cm$^{-1}$): 3470

EXAMPLE 1

(1R, 5S, 6S, 7R)-6-t-butyldiphenylsilyloxymethyl-7-hydroxybicyclo[3.3.0]octan-3-one (I)

To a mixture of (1R,5S,6S,7R)-3,3-ethylenedioxy-6-hydroxymethyl-7-(2'-tetrahydropyranyloxy)bicyclo[3.3.0]octane (II), (1.15 g, obtained from the processes of Referential Examples 1 to 3 described above), t-butylchlorodiphenylsilane (1.17 g) and N,N-dimethylformamide (6.0 ml) was added imidazole (0.66 g) and the mixture was stirred for 30 minutes at room temperature. Then the reaction mixture was poured into water and extracted with ether. The ether layer was washed with water and concentrated under reduced pressure. A mixture (20 ml) of acetic acid, water and tetrahydrofuran (3:1:1) was added to the residue and the mixture was stirred for 2 hours at 70° C. After cooling, the reaction mixture was poured into water and extracted with ethyl acetate. The ethyl acetate layer was successively washed with water, saturated aqueous sodium bicarbonate solution then saturated brine, and dried over magnesium sulfate. After filtration, the resulting ethyl acetate solution was concentrated under reduced pressure. The residue was purified by chromatography on silica gel (eluent: 20% ethyl acetate/hexane) to yield a crystalline compound (1.35 g). This was recrystallized twice from ethyl acetate/hexane (1:5) to yield the title compound (0.65 g) at higher optical purity.

m.p. 100°–101° C.

Specific rotation $[\alpha]_D^{21}+9.9°$ (c=1.95, CHCl$_3$).

Infrared absorption (KBr method) (cm$^{-1}$):3450, 1730, 1590. NMR spectrum (CDCl$_3$, 200 MHz):⊕7.69–7.64(m.4H), 7.46–7.37(m,6H), 4.21–4.10(m,1H), 3.82 (dd,J=10.1, 5.1Hz,1H), 3.67(dd,J=10.1, 7.6Hz,1H), 2.63–1.49(m,10H), 1.06(s,9H)

Determination of optical purity

A (R)-MTPA (α-methoxy-α-trifluoromethylphenylacetic acid) ester was prepared and subjected to a liquid chromatography with the following conditions.

Stationary phase: Nucleosil ®50–5
Column φ4.6x 250 mm
Eluent: Hexane-tetrahydrofuran (10:1)
Flow rate: 1.2 ml/min
Detection: at 254 nm
  Before recrystallization:
  Retention time 20.9 min. (80.9%)
    24.9 min. (19.1%)
  Optical purity: 61.8% e.e.
  After recrystallization:,Retention time
    20.9 min. (99.7%)
    24 9 min. (0.3%)
Optical purity: 99.4% e.e.

EXAMPLE 2

A solution of sucrose (15 g) in 0.1M phosphate buffer (pH7, 100 ml) was warmed to 30° C., and baker's yeast (7.0 g) was added, then shaken for 15 min at 30° C. An emulsion of (1SR,5RS)-2-ethoxycarbonyl-7,7-ethylenedioxybicyclo[3.3.0]octan-3-one (VIII) (498 mg) in 0.2% Triton X-100 (15 ml) was added and the mixture was shaken at 30° C. Sucrose (10 g) was added after 8 hours and successively sucrose (10 g) and baker's yeast (3.5 g) were added after 24 and 48 hours, then the mixture was shaken for 72 hours. Procedure similar to that of Referential Example 1 gave 109 mg of (1S,5R)-2-ethoxycarbonyl-7,7-ethylenedioxybicyclo-[3.3.0]octan-3-one (IV).

Specific rotation: $[\alpha]_D^{22}+19.9°$ (c=1.99, CHCl$_3$).

This compound was treated in the same manner as mentioned in Referential Examples 2 and 3 to yield (1R,5S,6S,7R)-3,3-ethylenedioxy-6-hydroxymethyl-7-(2'tetrahydropyranyloxy)bicyclo[(3.3.0]octane (II).

0.81 g of (1R,5S,6S,7R)-3,3-ethylenedioxy-6- hydroxymethyl-7-(2'-tetrahydropyranyloxy)bicyclo[3.3.0]octane (II) was used in a similar manner as Example 1 and recrystallized once to yield a 0.78 g of (1R,5S,6S,7R)-6-tert-butyldiphenylsilyloxymethyl-7-hydroxybicyclo[3.3.0]-octan-3-one (I).
Specific rotation: $[\alpha]_D^{21} +9.7°$ (c=1.83, CHCl$_3$)
Optical purity: determined as Example 1
Before recrystallization 79.0% e.e.
After recrystallization 98.8% e.e.

EXAMPLE 3

Each 100 ml medium (2% malt extract, 0.1% peptone, 2% glucose/purified water) placed in four Sakaguchi flasks was inoculated with one platinum loop of Saccharomyces cerivisiae NCYC 240, and the flasks were shaken at 30° C. for 64 hours to effect pre-cultivation. Two portions of the four pre-cultivated media were poured into two Erlenmeyer flasks each containing 1.8 l of the same media, and two flasks were shaken at 30 ° C. for 68 hours to effect cultivation. Cells collected by centrifugation were added to 100 ml of 0.1 M phosphate buffer containing glucose (10 g) at 30° C., and shaken for 15 minutes. To the resulting mixture was then added an emulsion of (1SR,5RS)-2-ethoxycarbonyl-7,7-ethylenedioxybicyclo[3.3.0]octan-3-one (VIII) (500 mg) in 0.2% Triton X-100 (15 ml) and the mixture was shaken at 30° C., to which glucose (10 g) after 6 hours and further glucose (5 g) after 22 hours were added and shaken for 50 hours. Cells were separated off by centrifugation, and a supernatant was saturated with sodium chloride and extracted three times with diethyl ether. The organic layer was washed with saturated brine, dried over magnesium sulfate and concentrated. The residue was purified by column chromatography (eluent: 20% (v/v) diethyl ether/hexane) to afford 185 mg of (1S,5R)-2-ethoxycarbonyl-7,7-ethylenedioxybicyclo[3.3.0]octan-3-one (IV).
Specific rotation: $[\alpha]_D^{21} +13.2°$ (c=2.12, CHCl$_3$)
This compound was treated in a similar manner as mentioned in Referential Examples 2 and 3 to yield (1R,5S,6S,7R)-3,3-ethylenedioxy-6-hydrxymethyl-7-(2'-tetrahydropyranyloxy)bicyclo[3.3.0]octane (II).
0.62 g of this compound was treated in a similar manner as mentioned in Example 1 and recrystallized twice to give 0.25 g of (1R,5S,6S,7R)-6-tert-butyl- diphenylsilyloxymethyl-7-hydroxybicyclo[3.3.0]octan-3one (I).
Specific rotation: $[\alpha]_D^{21} +9.7°$ (c=1.73, CHCl$_3$)
Optical purity: determined as Example 1
Before recrystallization 51.6% e.e.
After recrystallization 98.6% e.e.

EXAMPLE 4

Using Saccharomyces uvarum IFO 1225 cultivated similarly to Example 3, and 504 mg of (1SR,5RS)-2-ethoxycarbonyl-7,7-ethylenedioxybicyclo[3.3.0]octan-3-one (VIII), reaction was initiated in a similar procedure as mentioned in Referential Example 3. 10 g of glucose after 4 hours, 5 g after 19 hours, and 10 g after 153 hours were added and shaken for 167 hours. Aftertreatment of the reaction mixture in a similar manner as described in Example 3 gave 101 mg of (1S,5R)-2-ethoxycarbonyl-7,7-ethylenedioxybicyclo[3.3.0]octan-3-one (IV).
Specific rotation: $[\alpha]_D^{21} +18.3°$ (c=1.87, CHCl$_3$)
This compound was treated in a similar manner as described in Referential Examples 2 and 3 to yield (1R,5S,6S,7R)-3,3-ethylenedioxy-6-hydroxymethyl-7-(2'-tetrahydropyranyloxy)bicyclo[3.3.0]octane (II).
0.78 g of the compound (II) was treated in a similar manner as described in Example 1 and recrystallized once to yield 0.51 g of (1R,5S,6S,7R)-6-tert-butyldiphenyl- silyloxymethyl-7-hydroxybicyclo[3.3.0]octan-3-one (I).
Specific rotation: $[\alpha]_D^{21} +9.7°$ (c=1.73, CHCl$_3$)
Optical purity: determined as Example 1
Before recrystallization 73.6% e.e.
After recrystallization 98.6% e.e.

EXAMPLE 5

Using Saccharomyces carlsbergensis IFO 0565 cultivated similarly to Example 3 and 500 mg of (1SR,5RS)-2-ethoxycarbonyl-7,7-ethylenedioxybicyclo[3.3.0]octan-3-one (VIII), reaction was initiated in a similar manner as described in Referential Example 3. 10 g of glucose after 4 hours and 10 g after 23 hours were added and shaken for 68 hours. Aftertreatment of a reaction mixture in a similar manner as described in Referential Example 3 gave 219 mg of (1S,5R)-2-ethoxycarbonyl-7,7-ethylenedioxybicyclo[3.3.0]- octan-3-one (IV).
Specific rotation: $[\alpha]_D^{21} +12.6°$ (c=2.08, CHCl$_3$)
This compound was treated in a similar manner as described in Referential Examples 2 and 3 to yield (1R,5S,6S,7R)-3,3-ethylenedioxy-6-hydroxymethyl-7-(2'-tetrahydropyranyloxybicyclo[3.3.0.]octane (II).
0.52 g of this compound was treated in a similar manner as described in Example 1 and recrystallized twice to yield 0.18 g of (1R,5S,6S,7R)-6-tert-butyldiphenyl-silyloxy- methyl-7-hydroxybicyclo[3.3.0]octan-3-one (I).
Specific rotation: $[\alpha]_D^{21} +9.7°$ (c=1.68, CHCl$_3$)
Optical purity: determined as Example 1
Before recrystallization 50.6% e.e.
After recrystallization 99.0% e.e.

EXAMPLE 6

(1R,5S,6S,7R)-3,3-ethylenedioxy-6-hydroxymethyl-7-(2'-tetrahydropyranyloxy)bicyclo[3.3.0]octane (II)

A mixture of (1R,5S,6S,7R)-6-tert-butyldiphenyl-silyloxymethyl-7-hydroxybicyclo[3.3.0]octan-3-one (I) (2.00 g), ethylene glycol (6.08 g), p-toluenesulfonic acid (catalytic amount) and benzene (60 ml) was stirred under reflux with azeotropic removal of water for 1 hour. After cooling, a reaction mixture was poured into a saturated aqueous sodium bicarbonate solution and extracted with ethyl acetate. The ethyl acetate layer was washed with saturated brine and dried over magnesium sulfate. After ethyl acetate was evaporated under reduced pressure, to a residue were added dihydropyrane (0.62 g), pyridinium p-toluenesulfonate (0.12 g ) and anhydrous methylene chloride (20 ml) and a mixture was stirred at room temperature for 2 hours. The reaction solution was washed successively with saturated aqueous sodium bicarbonate solution and saturated brine and then dried over magnesium sulfate. After methylene chloride was evaporated off under reduced pressure, the residue was dissolved in 30 ml of tetrahydrofuran and 1.0 M solution of tetrabutylammonium fluoride (5.40 ml) in tetrahydrofuran was added and stirred at room temperature for 6 hours. Tetrahydrofura was distilled off under reduced pressure, then water was added to the residue and the mixture was extracted with ethyl acetate. The ethyl acetate layer was washed with water and saturated brine and then dried over magnesium sulfate. After ethyl acetate was distilled off under reduced pressure, the residue was purified by chromatography on silica gel (eluent: 33–60% (v/v) ethylacetate-n-hexane) to yield 1.33 g of the oily title compound. Infrared absorption (liquid-film method) (cm$^{-1}$): 3470 /NMR spectrum (CDCl$_3$: 200MHz): δ4.55–4.71(1H,m), 3.8–4.0 (4H,m), 3.4–3.8(5H,m), 2.72(1H,s), 1.3–2.5 (15H,m)

What is claimed is:

1. An optically active (1R,5S,6S,7R)-6-tert-butyldiphenylsilyloxymethyl-7-hydroxybicyclo[3.3.0]octan-3-one of formula (I)

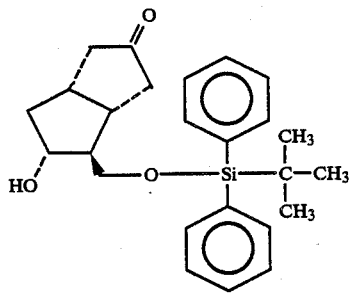

(I)

2. A process of preparing an optically active (1R,5S,6S,7R)-6-tert-butyldiphenylsilyloxymethyl-7-hydroxybicyclo[3.3.0]octan-3-one of formula (I)

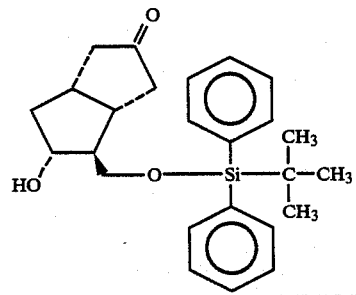

(I)

which comprises reacting (1R,5S,6S,7R)-3,3-ethylenedioxy-6-hydroxymethyl-7-(2'-tetrahydropyranyloxy)-bicyclo[3.3.0]octane of formula (II)

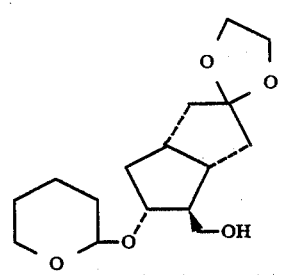

(II)

with tert-butylchlorodiphenylsilane in the presence of a base to form a compound of formula (III)

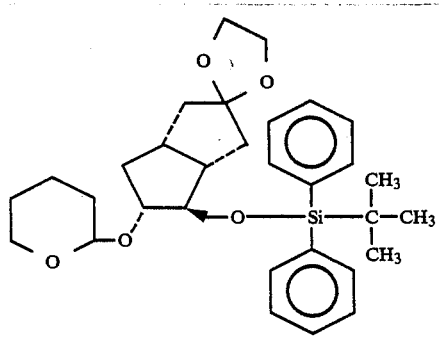

(III)

and removing the ethylenedioxy and tetrahydropyranyl groups of the resultant compound under an acid condition.

3. A process of preparing (1R,5S,7R)-3,3-ethylenedioxy-6-hydroxymethyl-7-(2'-tetrahydropyranyloxy)-bicyclo[3.3.0]octane having improved optical purity of formula (II)

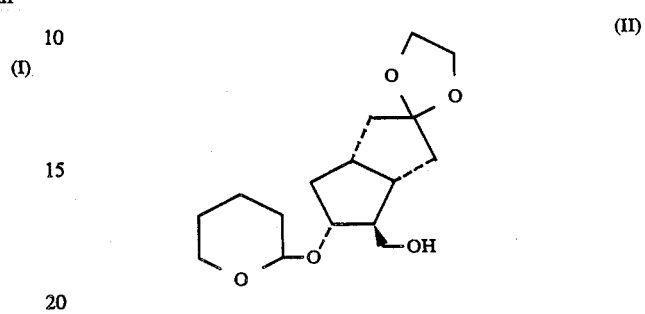

(II)

which comprises reacting (1R,5S,6S,7R)-3,3,-ethylenedioxy-6-hydroxymethyl-7-(2'-tetrahydropyranyloxy)-bicyclo[3.3.0]octane of formula (II)

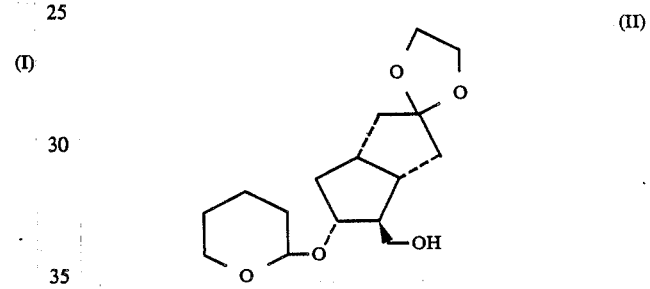

(II)

with tert-butylchlorodiphenylsilane in the presence of a base to form a compound of formula (III),

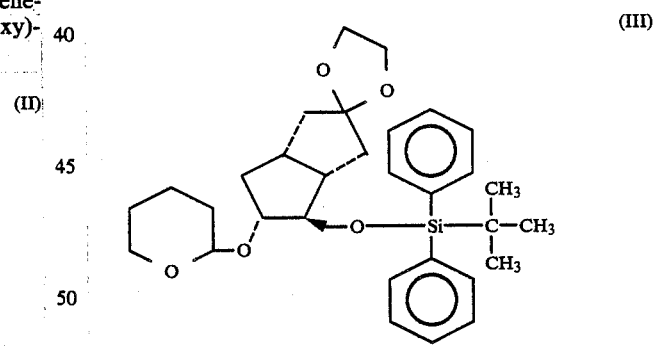

(III)

removing the ethylenedioxy and tetrahydropyranyl groups of the resultant compound under an acid condition to form (1R,5S,6S,7R)-6-tert-butyldiphenylsilyloxymethyl-7-hydroxy-bicyclo[3.3.0]octan-3-one of formula (I), subjecting the resultant compound to a recrystallization treatment to improve the optical purity, protecting the compound having improved optical purity at the 3- and 7-positions respectively with the ethylenedioxy and tetrahydropyranyl groups to form (1R,5S,6S,7R)-6-tert-butyldiphenylisilyloxymethyl-3,3-ethylenedioxy-7-(2'-tetrahydropyranyloxy)bicyclo [3.3.0]octane of formula (III) and removing the tert-butyldiphenylsilyl group of the resultant compound in the presence of a fluorine anion.

* * * * *

UNITED STATES PATENT AND TRADEMARK OFFICE
CERTIFICATE OF CORRECTION

PATENT NO. : 4,871,869

DATED : Oct. 3, 1989

INVENTOR(S) : MORI et al.

It is certified that error appears in the above-identified patent and that said Letters Patent is hereby corrected as shown below:

COLUMN 18, line 4 (CLAIM 3):

Reads: "(1R,5S,7R)"

Should Read: --(1R,5S,6S,7R)--

Signed and Sealed this

Twenty-third Day of October, 1990

Attest:

HARRY F. MANBECK, JR.

*Attesting Officer*      *Commissioner of Patents and Trademarks*